(12) United States Patent
Khamar et al.

(10) Patent No.: US 8,647,643 B2
(45) Date of Patent: Feb. 11, 2014

(54) FARNESOID-X-RECEPTOR ANTAGONIST AS A VACCINE ADJUVANT

(75) Inventors: Bakulesh Mafatlal Khamar, Ahmedabad (IN); Indravadan Ambalal Modi, Ahmedabad (IN); Rajiv Indravadan Modi, Ahmedabad (IN)

(73) Assignee: Cadila Pharmaceuticals, Ltd, Ahmedabad (IN)

( * ) Notice: Subject to any disclaimer, the term of this patent is extended or adjusted under 35 U.S.C. 154(b) by 131 days.

(21) Appl. No.: 13/121,449

(22) PCT Filed: Sep. 26, 2009

(86) PCT No.: PCT/IB2009/006950
§ 371 (c)(1),
(2), (4) Date: Mar. 29, 2011

(87) PCT Pub. No.: WO2010/035119
PCT Pub. Date: Apr. 1, 2010

(65) Prior Publication Data
US 2011/0182939 A1    Jul. 28, 2011

(30) Foreign Application Priority Data

Sep. 29, 2008  (IN) .......................... 2080/MUM/2008

(51) Int. Cl.
*A61K 39/00* (2006.01)
*A61K 39/02* (2006.01)
*A61K 39/12* (2006.01)
*A61K 39/002* (2006.01)
*A61K 47/28* (2006.01)

(52) U.S. Cl.
USPC .................... 424/278.1; 424/1.65; 424/184.1; 424/204.1; 424/234.1; 424/265.1; 424/274.1

(58) Field of Classification Search
None
See application file for complete search history.

(56) References Cited

U.S. PATENT DOCUMENTS

2006/0019907 A1* 1/2006 Aggarwal et al. ............... 514/26
2007/0218086 A1  9/2007 Tiollier

FOREIGN PATENT DOCUMENTS

WO    02/066612    8/2002
WO    2007/009194  1/2007

OTHER PUBLICATIONS

Tagawa et al. Development of an Enzyme Immunoassay for Serum 16-Dehydropregnenolone. 2001 Biol. Pharm. Bull. 24(8) 867-871.*
Suzuki T et al. The novel compounds that activate farnesoid X receptor: the diversity of their effects on gene expression. J Pharmacol Sci. Jul. 2008;107(3):285-94.*
International Search Report issued by the PCT on Mar. 16, 2010.

* cited by examiner

*Primary Examiner* — Louise Humphrey
*Assistant Examiner* — Nick Zou
(74) *Attorney, Agent, or Firm* — Burns & Levinson, LLP

(57) ABSTRACT

The invention provides novel adjuvants and pharmaceutical composition comprising of an adjuvant alone. The invention also provides novel vaccine compositions comprising of an antigen and a novel adjuvant. The novel adjuvant as per present invention is farnesoid-X-receptor (FXR) antagonist. The invention also relates to an adjuvant for variety of antigens. The adjuvant improves antibody production specific to incorporated antigen. The adjuvant also induces cell mediated immune response.

5 Claims, 6 Drawing Sheets

FARNESOID-X-RECEPTOR ANTAGONIST AS A VACCINE ADJUVANT

CROSS REFERENCE TO RELATED APPLICATION

This is a §371 U.S. National Stage of PCT Application No. PCT/IB2009/006950, filed Sep. 26, 2009, which was published in English under PCT Article 21(2), which in turn claims the benefit of Indian Application No. 2080/MUM/2008, filed on Sep. 29, 2008, which is incorporated by reference herein in its entirety.

FIELD OF INVENTION

The invention relates to adjuvants that can stimulate the mammalian immune system against disease specific antigen(s) and their pharmaceutical composition.

BACKGROUND OF INVENTION

Antigen specific immune response is concerned with the recognition and ultimate disposal of the antigen/immunogen in a highly discriminatory fashion. Specific immune responses are mediated through two types of effectors mechanisms. One is mediated by antibody produced by lymphocytes (humoral response) and the other is mediated by specially sensitized lymphocytes themselves (cell mediated immunity). The humoral responses are mainly responsible for providing prophylaxis against disease (Prophylactic vaccine). Prophylactic vaccines are administered in anticipation of a disease. Cell mediated immune responses are characterized by release of cytokine from immunized cells on exposure to an antigen. Cell mediated immunity is desirable for management of active disease (Therapeutic vaccine). Therapeutic vaccines are administered in presence of an active disease. The vaccine includes antigen(s) in a pharmaceutically acceptable carrier.

Antigens include immunogens, allergens. Antigens can be pathogens or varieties of material derived from pathogens like virus, bacteria, fungi, parasites. Tumor cells, mammalian cells and material derived from them can also be used as an antigen. The cells and organisms like virus, bacteria are used in the intact form e.g. Polio, BCG, Rabies etc. Chemical composition of antigen is widely variable and include peptides (of various kinds like plain peptide, poly peptides, Lipopetides etc), polysaccharides, polysaccharide congugates, lipids, glycolipids, carbohydrates, proteins, nucleic acids or antigen encoded into nucleic acids.

Antigens are categorized in varieties of ways. Some of them are described below.

Immunogen—The substance that provokes the immune response when introduced into the body. An immunogen is always a macromolecule (protein, polysaccharide). Its ability to stimulate the immune reaction depends on its commonness to the host, molecular size, chemical composition and heterogeneity (e.g. similar to amino acids in a protein).

Allergen—An allergen is a substance that causes the allergic reaction. It can be ingested, inhaled, injected or comes into contact with skin.

(II) Antigens can be Classified in Order of their Origins.

Exogenous antigens—Exogenous antigens are antigens that have entered the body from the outside, for example by inhalation, ingestion, or injection.

Endogenous antigens—Endogenous antigens are antigens that have been generated within the cell, as a result of normal cell metabolism, or because of viral or intracellular bacterial infection. The fragments are then presented on the cell surface in the complex with class I histocompatibility molecules.

(III) Types of Antigen

Tumor antigens—Tumor antigens are those antigens that are present on the surface of tumor cells. These antigens can sometimes be presented only by tumor cells and never by the normal ones. In this case, they are called tumor-specific antigens and typically result from a tumor specific mutation. More common are antigens that are presented by tumor cells and normal cells, and they are called tumor-associated antigens. Cytotoxic T lymphocytes that recognize these antigens may be able to destroy the tumor cells before they proliferate or metastasize. Tumor antigens can also be on the surface of the tumor in the form of, for example, a mutated receptor, in which case they will be recognized by B cells.

Pathogen associated antigens—Antigens are derived from pathogens like virus, Bacteria, fungus, parasites e.g. rabies, Hepatitis B, mump, measles, tetanus, diphtheria etc.

Production of Antigen

Antigens can be produced by recombinant technologies, extraction methods, chemical synthesis, fermentation etc. It can be in the form of a compound or an organism which is natural or genetically modified or a fraction of an organism, which is naturally occurring or genetically modified. Nucleic acids are increasingly being developed and identified as antigens, as in DNA vaccines. Antigens can be administered in the form of naked antigens or encapsulated, coated form, conjugated, mixed, coupled and/or formulated with adjuvant.

Most of the vaccines when applied alone does not produce an adequate immune stimulus. Adjuvants are added to antigen in vaccine composition to enhance the body's immune response to specific antigens of the vaccine. Adjuvants are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Adjuvant can also act by activating antigen presenting cells.

Adjuvants are used to,

Increase antibody response in magnitude or function (e.g. avidity)

Cell mediated immune response

Reduction in antigen dose

Time of mounting response (Faster response, sustained response etc.)

Induction of mucosal immunity

Improve seroconversion and/or seroprotection rates.

One of the approved adjuvants for human use is alum. The adjuvant activity of alum was first discovered in 1926 by Glenny (*Chemistry and Industry*, Jun. 15, 1926; *J. Path. Bacterial*, 34, 267). Aluminum salts (alum) have been useful for some vaccines like hepatitis B, diphtheria, tetanus, toxoid etc., but not useful for others like rabies MMR, typhoid etc. It fails to induce cell-mediated immunity. Aluminum hydroxide and aluminum phosphate is collectively commonly referred to as alum. Reports indicate that alum failed to improve the effectiveness of whooping cough and typhoid vaccines and provided only a slight effect with adenovirus vaccines.

A wide range of other materials are also known to have adjuvant activity provokes potent immune responses to antigens. These includes but not limited to, Saponins like QS21, ISCOMS Saponins complexed to membrane protein antigens (immune stimulating complexes), Pluronic polymers with mineral oil, Killed *Mycobacteria* in mineral oil, a water-in-mineral-oil emulsion which contains killed/dried mycobacteria in the oil phase, a weaker formulation without the mycobacteria, Freund's complete adjuvant, Freund's incomplete adjuvant, Bacterial products, such as muramyl dipeptide (MDP) and lipopolysaccharide (LPS), MPL as well as lipid A, Liposomes, a membrane active glucoside extracted from the tree *Quillia saponaria*, nonionic block copolymer surfactants, Non metabolised synthetic molecules which tend to bind proteins to cell surfaces; ISCOMS, Infectious particles Oil-in-water emulsions—MF59

CpG (Oligonucleotides)—TLR agonists

Other TLR agonists like imiquimod

Immunopeptides

Complete Freund's adjuvant (CFA) is a powerful immunostimulatory agent that has been successfully used with many antigens on an experimental basis. CFA includes three components: a mineral oil, an emulsifying agent, and killed *Mycobacterium tuberculosis*. Aqueous antigen solutions are mixed with these components to create a water-in-oil emulsion. Although effective as adjuvant, CFA causes severe side effects e.g. pain, abscess formation, fever etc. CFA, therefore, is not used in preparation of commercial vaccines.

Incomplete Freund's adjuvant (IFA) is similar to CFA but does not include the bacterial component. It is a oil in water emulsion. However, evidence indicates that both the oil and emulsifier used in IFA can cause tumors in mice. Muramyl dipeptide (MDP) has been found to be the minimal unit of the mycobacterial cell wall complex that generates the adjuvant activity observed with CFA. e.g., Ellouz et al., Biochem. Biophys. Res. Commun. (1974) 59:1317.

Several synthetic analogs of MDP have been generated that exhibit a wide range of adjuvant potency and side effects (Chedid et al., Prog. Allergy (1978) 25:63). Representative analogs of MDP include threonyl derivatives of MDP (Byars et al., Vaccine (1987) 5:223), n-butyl derivatives of MDP (Chedid et al., Infect. Imrriun. 35:417), and a lipophilic derivative of a muramyl tripeptide (Gisler et al., in Immunomodulations of Microbial Products and Related Synthetic Compounds (1981) Y. Yamamura and S. Kotani, eds., Excerpta Medica, Amsterdam, p. 167). One lipophilic derivative of MDP is N-acetylmurarnyl-L-alanyl-D-isogluatminyl-L-alanine-2-(1'-2'dipalmitoyl-sn-glycero-3-hydroxyphosphoryloxy)-ethylamine (MTP-PE). The MTP-PE itself is able to act as an emulsifying agent to generate stable oil-in-water emulsions. MTP-PE has been used in an emulsion of squalene with TWEEN 80, termed MTP-PE-LO (low oil), to deliver the herpes simplex virus gD antigen with effective results (Sanchez-Pescador et al., J. Immunol. (1988) 141: 1720-1727), albeit poor physical stability.

Synthetic polymers are evaluated as adjuvants. These include the homo- and copolymers of lactic and glycolic acid, which have been used to produce micro-spheres that encapsulate antigens (see Eldridge et al., MoI. Immunol. 28:287-294 (1993)).

Nonionic block copolymers are another synthetic adjuvant being evaluated. Adjuvant effects are investigated for low molecular weight copolymers in oil-based emulsions and for high molecular weight copolymers in aqueous formulations (Todd et al., Vaccine 15:564-570 (1997)).

The adjuvants using whole cells like insect cells (*S. frugiperda*) U.S. Pat. No. 6,224,882 are known. The insects or the insect cells infected with some of the insect viruses/infectious agent or any other type of infection, also it is not yet possible to identify that which insect/insect cell is infected and which not hence the use of these can result in low production and a possible threat of transmission of disease to human (WHO report January 2005).

In an article published in Vaccine (1999) 17; 2446-2452, *Bacillus* of Calmette-Guer̈ṅ (BCG) is used as adjuvant to rabies vaccination in mice. The experimental results show no improvement in serum neutralizing antibody titers in-group of mice immunized with BCG as adjuvant compared to plain vaccine.

U.S. Pat. No. 6,355,414 describes accmannan polysaccharide as adjuvant. U.S. Pat. No. 6,306,404 describes adjuvant & vaccine compositions of mono phosphoryl lipid A, sugar and optionally an amine-based surfactant. U.S. Pat. No. 6,231,859 describes saponin combination as adjuvant. Saponin adjuvants have high systemic toxicities, like haemolysis. The U.S. Pat. No. 6,060,068 describes interleakin-2 as adjuvant to vaccines. U.S. Pat. No. 6,355,256 describes QS-21 & IL-12 as adjuvants.

PCT application WO/2006/114680 discloses *Mycobacterium* w as adjuvant with pharmaceutically acceptable carrier and its uses. U.S. Pat. Nos. 6,103,697, 6,228,373 & 6,228,374 describes peptides as adjuvants. JP 11106351, JP 9268130 & AU 780054 describe oil adjuvants. U.S. Pat. No. 6,383,498 discloses compositions of vaccine wherein Neuraminidase and galactose oxidase together are a vaccine adjuvant. U.S. Pat. No. 7,579,009 discloses an immune modulator composition and/or pharmaceutical composition comprising whole cell of a bacterium. U.S. Pat. No. 6,375,945 discloses adjuvant composition comprising a mixture of a saponin adjuvants and use of there compositions in prophylactic and therapeutic applications, particularly in vaccine including cancer vaccines. U.S. Pat. No. 6,306,404 discloses adjuvant and vaccine composition of monophosphoryl lipid. U.S. Pat. No. 7,488,490 discloses unmethylated CpG dinucleotide (CpG ODN) and a non-nucleic acid adjuvant. But in all these adjuvants are not demonstrated with wide variety of antigens and mammals.

The above mentioned adjuvants are at various stages of development. There is still a need to have novel adjuvants to provide novel vaccine with reduced antigen, reduced frequency, increased immunogenic potential. Currently available adjuvants are outcome of painstaking research in absence of a method to identify potential compound with adjuvant properties. It is long standing need of the industry to provide adjuvants that are free of above-mentioned side effects.

REFERENCES

Essential Immunology, Eight Edition Ivan Roitt, Black well Scientific publication.

Vaccines, Third edition. S. Plotkein W. Orenstein, W.B.Saunder's company

Vaccines—Prospects & perspectives Harminder sigh, rajesh Bhatia, forward publishing company, Delhi Immunotherapy of cancer Mary L. Disis, Humana press, Totowa, N.J., USA.

DNA vaccine Douglas B. Lowrie, Robert G. Whalen, Humana press, Totowa N.J., USA.

Handbook of cancer vaccines Micheal A. Morse, Timothy M Clay, H. Kiva Lyerly. Humana press Totowa N.J., USA.

Cellular Microbiology Bian Henderson, Micheal Wilson, John wiley & sons.

SUMMARY OF INVENTION

The main object of invention is to provide adjuvants that can stimulate the mammalian immune system to provide antigen(s) specific immune response.

Yet another object of invention is to provide composition consisting novel adjuvants as per this invention for administration to mammals.

Yet another object of invention is to provide vaccine composition with improved efficacy.

Yet another object of invention is to provide adjuvants to improve efficacy of vaccines.

Yet another object of invention is to provide adjuvants to pre-pone the immune response generated by vaccines Yet another object of invention is to provide adjuvants for generating sustained immune responses with vaccines.

Yet another object of invention is to provide adjuvants for generating cell mediated immune responses.

Yet another object of invention is to provide adjuvants for generating antigen specific neutralizing antibodies.

Yet another object of present invention is to provide sustained seroprotection with minimal number of immunization.

Yet another object of present invention is to provide sustained seroprotection with minimal immunization.

DETAILED DESCRIPTION

Figure 1:
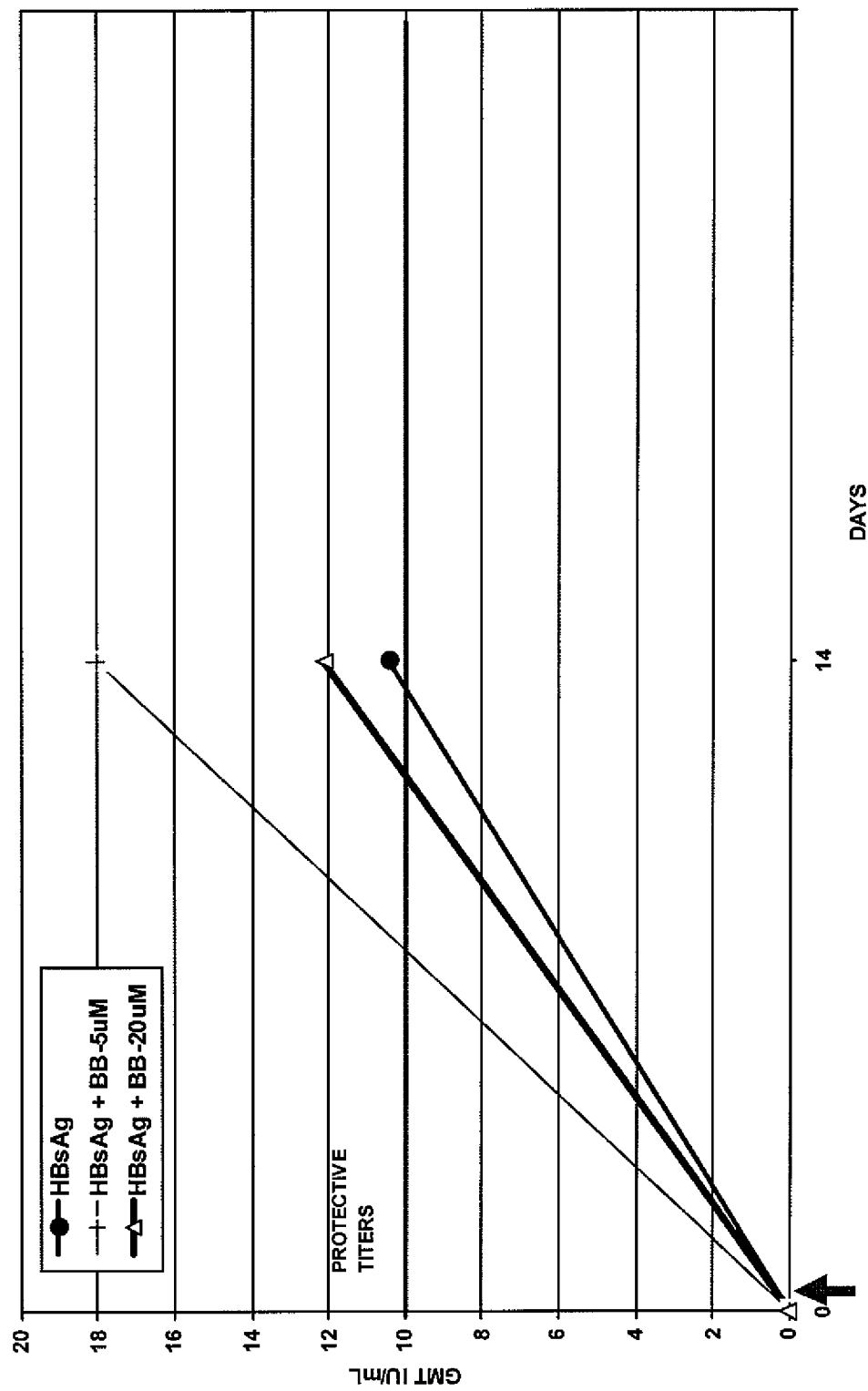
FIG. 1 Neutralising antibody titers following immunization with Hepatitis-B vaccine as per present invention. (Early rise in antibody titer leads to sero-protection)

Farnesoid X receptor (FXR) is expressed at high levels in the liver and small intestine, in which it regulates bile acid homeostasis on activation by these natural ligands. Consequently, the role of FXR is to protect the liver from the deleterious effect of bile acid overloading by inhibiting their biosynthesis and stimulating their excretion. Some of the FXR antagonists are guggulipid, guggulsterones, 3β-Acetoxypregna-5,16-dien-20-one (16-DPA), 4,16-Dienpregna-3,20-dione, 3β-Actoxypregna-5-en-20-one, 3β-Hydroxypregna-5-en-20-one,5,16-Dien-pregnane-3,20-diol, 5,17(20)-Dien-pregna-3,16-diol-diacetate, 5,17(20)-Dien-pregna-3,16-diol, 3β-Hydroxypregna-5,16-dien-20-one, 7-(2-Hexyloxy-3,5-diisopropyl-phenyl)-3-methyl-octa-2,4,6-trienoic acid, Z-Guggulsterone, [4,17(20)-Cis-pregnadiene-3,16-dione], E-Guggulsterone [4,17(20)-Cis-pregnadiene-3,16-dione] etc. The structures of these compounds are as under:

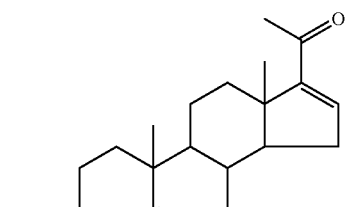

3β-Acetoxypregna-5,16-dien-20-one (16-DPA)

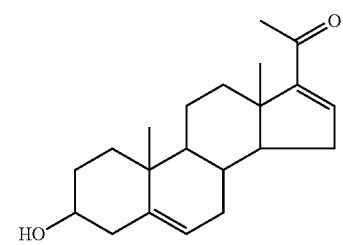

3β-Hydroxypregna-5,16-dien-20-one

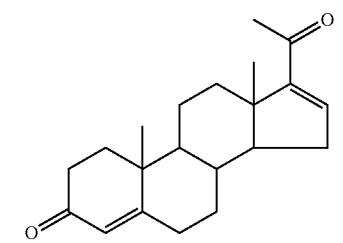

4,16-Dienpregna-3,20-dione

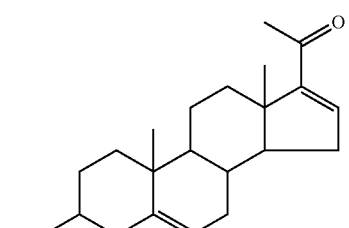

3β-Actoxypregna-5-en-20-one

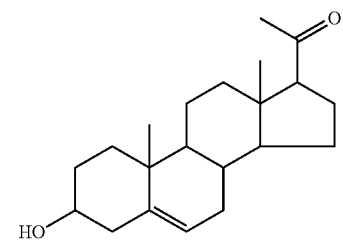

3β-Hydroxypregna-5-en-20-one

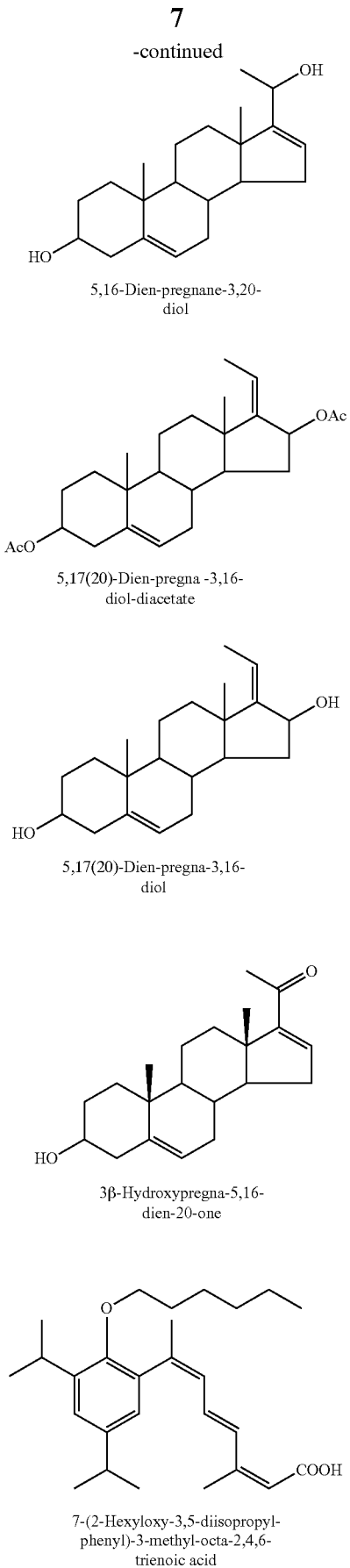

5,16-Dien-pregnane-3,20-diol 5,17(20)-Dien-pregna-3,16-diol-diacetate 5,17(20)-Dien-pregna-3,16-diol 3β-Hydroxypregna-5,16-dien-20-one 7-(2-Hexyloxy-3,5-diisopropyl-phenyl)-3-methyl-octa-2,4,6-trienoic acid

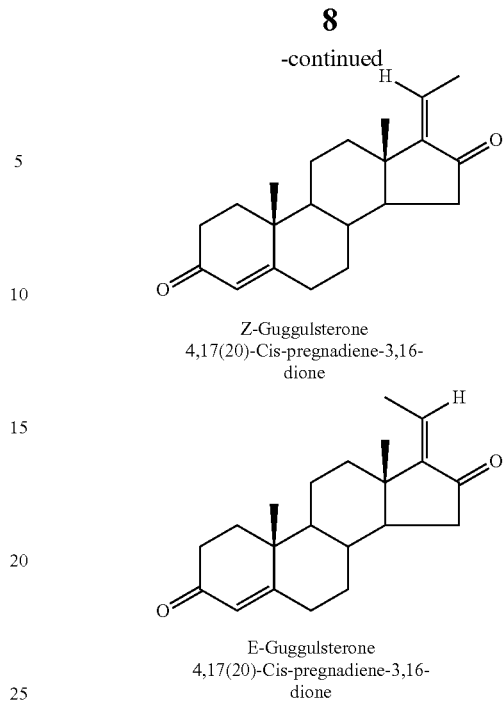

Z-Guggulsterone
4,17(20)-Cis-pregnadiene-3,16-dione

E-Guggulsterone
4,17(20)-Cis-pregnadiene-3,16-dione

FXR antagonists are known in the art to have hypolipaemic effects.

Surprisingly as per present invention it is observed that FXR antagonists act as vaccine adjuvant.

The vaccine is prepared by mixing FXR antagonists and an antigen. FXR antagonists typically are water insoluble. For the purpose of present invention they may be suspended in to liquid containing antigen. They may be formulated as an emulsion for incorporation into vaccine. They may be incorporated into liposomes with or without antigens. They can be incorporated as powder. The vaccine according to the invention consequently contains FXR antagonists as good adjuvant along with antigen, excipients, stabilizers and pharmaceutical carriers as per requirement of pharmaceutical composition.

FXR antagonist can be obtained from natural sources or prepared efficiently and economically through processes used for manufacturing of synthetic chemicals, as a synthetic adjuvant that is chemically synthesized from defined starting materials to obtain a chemically defined product that exhibits qualitative and quantitative batch-to-batch consistency. FXR antagonist offers unprecedented benefits including improved product quality control. Thus, the invention offers further advantages in terms of ease of synthesis and quality control of the product.

According to present invention pharmaceutical compositions comprising of an adjuvant are disclosed to alter immunological response in a host.

To determine immuno stimulatory/adjuvant properties of compounds different immunoanalysis methods can be employed. Determination of the induction of an immune response by the vaccines of the present invention may be established by any of a number of well known immunological assays with which those having ordinary skill in the art will be readily familiar. Such assays include, but need not be limited to, to in vivo or in vitro determination of soluble antibodies; soluble mediators such as cytokines, lymphokines, chemokines, cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, Mass.; Mishell and Shigii (eds.) Selected Methods in Cellular Immunology, 1979 Freeman Publishing, San Francisco, Calif.; Green and Reed, 1998 Science 281:1309 and references cited therein.).

Detection of cellular immune response may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive immune cells are exposed. Other ways to detect immune cell proliferation include measuring increases in Interferon-gamma (IFN-g) producing cells, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of immune cells that can respond to a particular antigen may be quantified.

Detection of antigen-specific antibody production may be achieved, for example, by assaying a sample (e.g., an immunoglobulin containing sample such as serum, plasma or blood) from a host treated with a vaccine according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems, Minneapolis, Minn.). An immune response may be detected by measuring in vivo protection from disease in an appropriate animal model.

For the purpose of the present invention, the term "antigen" is intended to mean any an antigen or antigenic composition which can be used in a vaccine and capable of eliciting an immune response against a human pathogen.

For the purpose of present invention the antigen or antigenic composition is selected from peptide, protein, carbohydrate antigens, bacterial, fungal, protozoal, viral antigen or parasites, polypeptides, cells, cell extracts, polysaccharides, polysaccharide conjugates, lipids, glycolipids, viruses, viral extracts, virus like particles, nuclear material or antigen encoded in nucleic acids.

FXR antagonist as per present invention provides adjuvant effect against various types of antigens/vaccines like whole live organism, killed or inactivated organisms, spilt vaccine, subunit vaccines, cancer vaccines etc.

According to present invention mammals when administered with pharmaceutical composition containing antigen/s with FXR antagonists an adjuvant results in a faster rise in antibody titer which are higher and long lasting compared to when FXR antagonists are not used.

FXR antagonist as per present invention is ranging from 10 nM to 1 mM. The better results are obtained with FXR antagonist ranging from 1 µM to 100 µM.

3β-hydroxy-5,16-pregnadien-20-one ($C_{21}H_{30}O_2$) is potent FXR antagonist (here in after called as BB), is found to have adjuvant properties like others in the FXR antagonist class of compounds. BB is water insoluble. The structure of 3βHydroxy-5,16-pregnadien-20-one (BB) is as under:

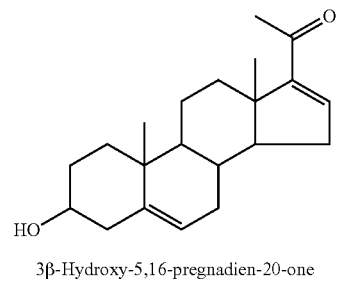

3β-Hydroxy-5,16-pregnadien-20-one

Vaccine

Vaccines of the present invention may be used for the prophylaxis or for therapy of disease. Further the effect of adjuvants as immune enhancer is observed for therapeutic vaccine and prophylactic vaccine. The vaccine compositions as per present invention contains the same adjuvant and sub classified vaccine/antigen such as live whole virus vaccines, killed whole virus vaccines, subunit vaccines comprising purified or recombinant viral antigen, recombinant virus vaccines, anti-idiotype antibodies, DNA vaccines and like.

The following examples of compositions are as per present invention without preservatives. If required to produce multidose units, the preservatives can be added. For improved stability, whenever required the composition can be in the form of a dry powder. Dry powder may be obtained by lyophilisation and/or freeze drying of composition before or after adding adjuvant. When nature of antigen requires it to be in dry form the adjuvant may be provided in a diluent.

EXAMPLES

Example I

Each 1.0 ml of composition contains:

| | |
|---|---|
| Recombinant Hepatitis B surface antigen | 10 µg |
| 3βHydroxy-5,16-pregnadien-20-one ($C_{21}H_{30}O_2$) | 5 µM |
| Water for injection I.P. | q.s. to 1.0 ml |

Example II

Each 1.0 ml of composition contains:

| | |
|---|---|
| Recombinant Hepatitis B surface antigen | 10 µg |
| 3βHydroxy-5,16-pregnadien-20-one ($C_{21}H_{30}O_2$) | 20 µM |
| Normal Saline | q.s. to 1.0 ml |

Example III

Each 1.0 ml of composition contains:

| | |
|---|---|
| Recombinant Hepatitis B surface antigen | 10 μg |
| 3βHydroxy-5,16-pregnadien-20-one ($C_{21}H_{30}O_2$) | 50 μM |
| Water for injection I.P. | q.s. to 1.0 ml |

Example IV

Each 1.0 ml of composition contains:

| | |
|---|---|
| Recombinant Hepatitis B surface antigen | 20 μg |
| 3β-Acetoxypregna-5,16-dien-20-one(16-DPA) | 10 μM |
| Normal Saline | q.s. to 1.0 ml |

Example V

Each 1.0 ml of composition contains:

| | |
|---|---|
| rDNA coding Rabies antigen | 100 uG |
| 3βHydroxy-5,16-pregnadien-20-one (C21H30O2) | 5 μM |
| Water for injection I.P. | q.s. to 1.0 ml |

Example VI

Each 1.0 ml of composition contains:

| | |
|---|---|
| rDNA coding Rabies antigen | 100 uG |
| 4,16-Dienpregna-3,20-dione | 15 μM |
| Water for injection I.P. | q.s. to 1.0 ml |

Example VII

Each 1.0 ml of composition contains:

| | |
|---|---|
| Inactivated rabies virus (Rabipur) antigen | 2.5 IU |
| 3βHydroxy-5,16-pregnadien-20-one ($C_{21}H_{30}O_2$) | 20 μM |
| Normal Saline | q.s. to 1.0 ml |

Example VIII

Each 1.0 ml of composition contains:

| | |
|---|---|
| Inactivated rabies virus (Rabipur) antigen | 2.5 IU |
| 3βHydroxy-5,16-pregnadien-20-one ($C_{21}H_{30}O_2$) | 10 μM |
| Normal Saline | q.s. to 1.0 ml |

Example IX

Each 1.0 ml of composition contains:

| | |
|---|---|
| Inactivated rabies virus (Rabipur) antigen | 2.5 IU |
| 3β-Hydroxypregna-5,16-dien-20-one | 1 μM |
| Normal Saline | q.s. to 1.0 ml |

Example X

Each 1.0 ml of composition contains:

| | |
|---|---|
| Cancer cell (Mia-Pa—Ca) | $10^6$ |
| 3β-Hydroxypregna-5,16-dien-20-one | 10 μM |
| Normal Saline | q.s. to 1.0 ml |

Example XI

Each 1.0 ml of composition contains:

| | |
|---|---|
| Cancer cell ($SPO_2$) | $10^5$ |
| 5,17(20)-Dien-pregna-3,16-diol-diacetate | 20 μM |
| Normal Saline | q.s. to 1.0 ml |

Example XII

Each 1.0 ml of composition contains:

| | |
|---|---|
| Cancer cell (Panc-1) | $10^7$ |
| 4,16-Dienpregna-3,20-dione | 5 μM |
| Normal Saline | q.s. to 1.0 ml |

Example XIII

Each 1.0 ml of composition contains:

| | |
|---|---|
| Inavtivated Hepatitis A virus | $10^5$ |
| 5,17(20)-Dien-pregna-3,16-diol-diacetate | 20 μM |
| Normal Saline | q.s. to 1.0 ml |

Example XIV

Each 1.0 ml of composition contains:

| | |
|---|---|
| *Bordetella partasis* | 4000 m org |
| Diptheria toxoid | 50 Lf |
| Tetanus toxoid | 10 Lf |
| 5,17(20)-Dien-pregna-3,16-diol | 15 μM |
| Normal Saline | q.s. to 1.0 ml |

Example XV

Each 1.0 ml of composition contains:

| | |
|---|---|
| H influenza saccharide | 10 µg |
| [4,17(20)-Cis-pregnadiene-3,16-dione] | 15 µM |
| Normal Saline | q.s. to 1.0 ml |

Example XVI

Each 1.0 ml of seasonal influenza composition contains:

| | |
|---|---|
| H1N1 pandemic strain [Ca/04] | 15 µg of HA |
| H1N1 virus [Br/59] | 15 µg of HA |
| H3N2 virus [Br/10] | 15 µg of HA |
| Z-Guggulsterone | 5 µM |
| Normal Saline | q.s. to 1.0 ml |

Example XVII

Each 1.0 ml of composition contains:

| | |
|---|---|
| Purified VI capsulan polysaccharide of S. TYphi | 2.5 µg |
| 4,16-Dienpregna-3,20-dione | 10 µM |
| Normal Saline | q.s. to 1.0 ml |

The formulations as described above can be produced for different antigen comprising FXR antagonist as adjuvant in the required dose volumes and concentrations. The following examples provide general scheme of incorporating adjuvants of present invention to various antigens.

Example XVII

10 µg of Recombinant Hepatitis B surface antigen with FXR antagonist as an adjuvant:

TABLE 01

| FXR antagonist | Concentration | | | | |
|---|---|---|---|---|---|
| 3β-Hydroxy-5,16-pregnadien-20-one | 5 µM | 10 µM | — | 20 µM | 50 µM |
| 3β-Acetoxypregna-5,16-dien-20-one(16-DPA) | — | 10 µM | — | 20 µM | — |
| 4,16-Dienpregna-3,20-dione | 5 µM | — | 15 µM | — | — |
| 3β-Hydroxypregna-5,16-dien-20-one | 5 µM | — | 15 µM | — | 50 µM |

Example XVIII

20 µg of Recombinant Hepatitis B surface antigen with FXR antagonist as an adjuvant:

TABLE 02

| FXR antagonist | Concentration | | | | |
|---|---|---|---|---|---|
| 3β-Hydroxypregna-5-en-20-one | 5 µM | 10 µM | — | — | — |
| 5,17(20)-Dien-pregna-3,16-diol-diacetate | — | 10 µM | 15 µM | — | 50 µM |
| 3β-Actoxypregna-5-en-20-one | — | 10 µM | 15 µM | — | 50 µM |
| Z-Guggulsterone | 5 µM | 10 µM | — | 20 µM | 50 µM |
| 5,17(20)-Dien-pregna-3,16-diol | 5 µM | 10 µM | — | — | — |
| [4,17(20)-Cis-pregnadiene-3,16-dione] | — | 10 µM | — | — | 40 µM |
| [4,17(20)-Trans-pregnadiene-3,16-dione] | — | 10 µM | — | 20 µM | 40 µM |

Example XIX 2.5 IU of Inactivated rabies virus (Rabipur) antigen with FXR antagonist as an adjuvant:

TABLE 03

| FXR antagonist | Concentration | | | | |
|---|---|---|---|---|---|
| Guggulipid | 1 µM | — | 15 µM | — | 50 µM |
| 3β-Acetoxypregna-5,16-dien-20-one(16-DPA) | 5 µM | 10 µM | — | 20 µM | — |
| 4,16-Dienpregna-3,20-dione | — | 10 µM | — | 20 µM | — |
| 3β-Hydroxy-5,16-pregnadien-20-one | 5 µM | 10 µM | 15 µM | 20 µM | 50 µM |
| 5,17(20)-Dien-pregna-3,16-diol | 5 µM | — | — | 20 µM | — |
| 3β-Hydroxypregna-5,16-dien-20-one | 1 µM | 10 µM | 25 µM | — | 50 µM |
| [4,17(20)-Cis-pregnadiene-3,16-dione] | 5 µM | — | 15 µM | — | 50 µM |
| E-Guggulsterone | — | 10 µM | 15 µM | 20 µM | — |
| [4,17(20)-Trans-pregnadiene-3,16-dione] | 1 µM | 5 µM | 10 µM | — | 50 µM |

Example XX $10^7$ of Cancer cells (Mia-paca 2) antigen with FXR antagonist as an adjuvant:

TABLE 04

| FXR antagonist | Concentration | | | | |
|---|---|---|---|---|---|
| 3β-Hydroxy-5,16-pregnadien-20-one | 5 μM | — | — | — | 50 μM |
| 3β-Acetoxypregna-5,16-dien-20-one(16-DPA) | — | 10 μM | — | 20 μM | — |
| 4,16-Dienpregna-3,20-dione | 5 μM | 10 μM | — | 20 μM | 50 μM |

Example XXI $10^6$ of Cancer cells (Mia-paca 2) antigen with FXR antagonist as an adjuvant:

TABLE 05

| FXR antagonist | Concentration | | | | |
|---|---|---|---|---|---|
| 3β-Actoxypregna-5-en-20-one | — | 10 μM | 15 μM | 20 μM | 50 μM |
| 5,17(20)-Dien-pregna-3,16-diol-diacetate | — | 10 μM | — | 20 μM | — |
| 3β-Hydroxypregna-5,16-dien-20-one | — | 10 μM | — | 20 μM | 50 μM |

Example XXII $10^5$ of Cancer cells (Mia-paca 2) antigen with FXR antagonist as an adjuvant:

TABLE 06

| FXR antagonist | Concentration | | | | |
|---|---|---|---|---|---|
| [4,17(20)-Trans-pregnadiene-3,16-dione] | 5 μM | — | 15 μM | 20 μM | 40 μM |
| [4,17(20)-Cis-pregnadiene-3,16-dione] | 5 μM | — | 15 μM | 20 μM | 40 μM |

Example XXIII 100 uG of rDNA (Encoding rabies antigen) antigen with FXR antagonist as an adjuvant:

TABLE 07

| FXR antagonist | Concentration | | | | |
|---|---|---|---|---|---|
| 3β-Hydroxy-5,16-pregnadien-20-one | 5 μM | 10 μM | — | 20 μM | 50 μM |
| [4,17(20)-Cis-pregnadiene-3,16-dione] | — | 10 μM | 15 μM | — | — |
| 4,16-Dienpregna-3,20-dione | 5 μM | — | 15 μM | 20 μM | — |
| 5,16-Dien-pregnane-3,20-diol | 5 μM | 10 μM | — | 20 μM | 50 μM |
| 7-(2-Hexyloxy-3,5-diisopropyl-phenyl)-3-methyl-octa-2,4,6-trienoic acid | 5 μM | 10 μM | — | 20 μM | — |

The adjuvant property of present invention is analysed by assessing the antibody response to the associated antigen as well as cell mediated immune response. The following examples describes the enhance immune response using FXR antagonists as an adjuvant along with antigens. Some of these are described herein below to provide the overview of the invention but are not limiting the scope of present invention.

Example 1

Wistar rats/3 per group were immunized with rHBsAg antigen mixed with 5 μM and 20 μM of BB. Each Rat was injected with 10 μg, on day 0, intramuscular injection. Anti-HBsAg antibodies were detected in individual rat serum at every 14 days interval. BB-50 uM BB-5 uM are lead adjuvants. The results of this study are presented in FIG. 1.

Example 2

Figure 2:
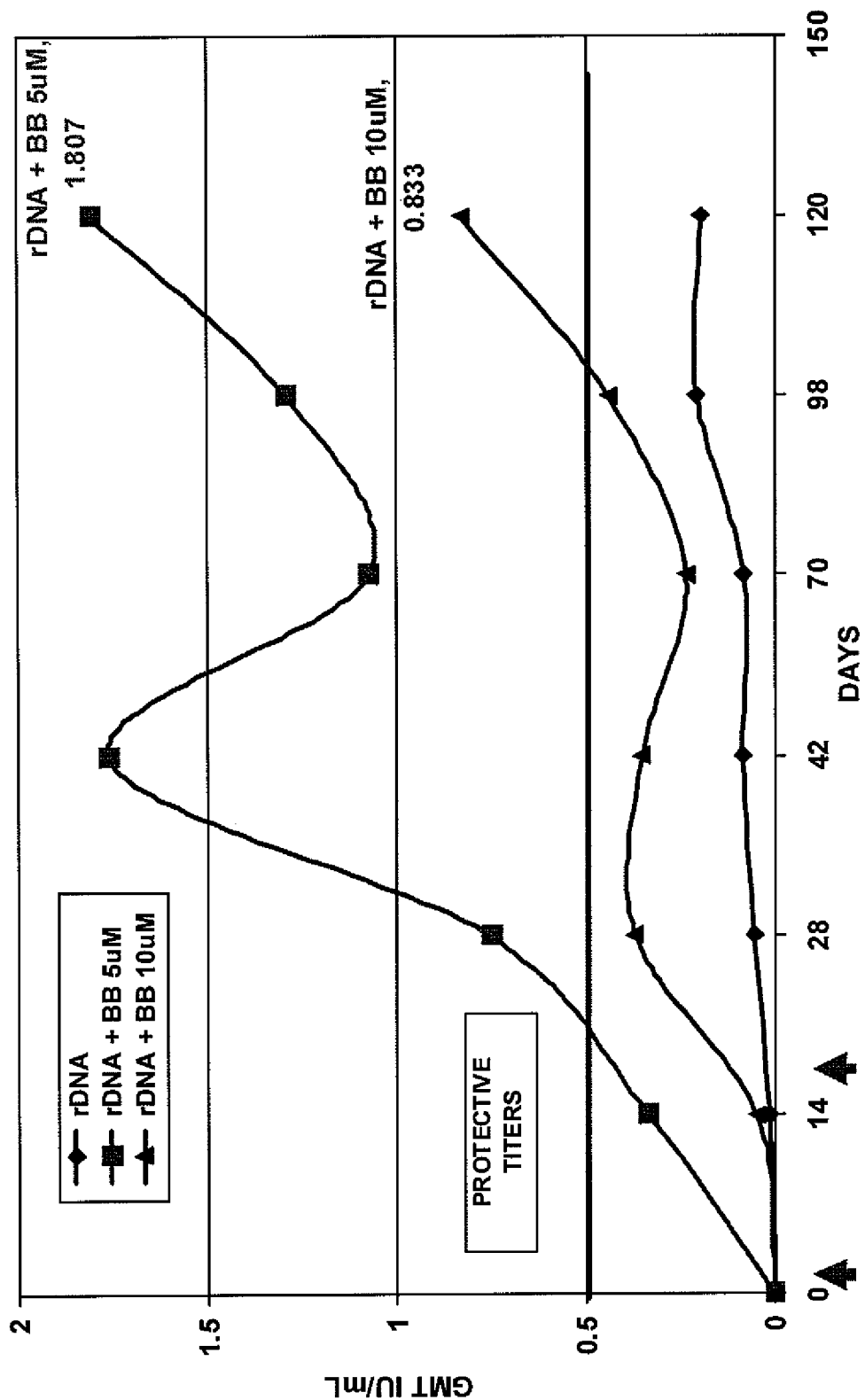
FIG. 2 Neutralising antibody titers following immunization with rDNA encoding Rabies vaccine as per present invention. (Early, higher and sustained antibody titer leading to sero-protection which is maintained)

5 Swiss albino mice per group were randomized and immunized with 100 uG of rDNA coding Rabies antigen on Day 0 and day 14. rDNA with 5 μM and 10 μM of BB provides protective antibody titers on day 28 after $1^{st}$ dose of vaccine. The titers remained protective for about 100 days. The results of this study are presented in FIG. 2.

Example 3

Figure 3:
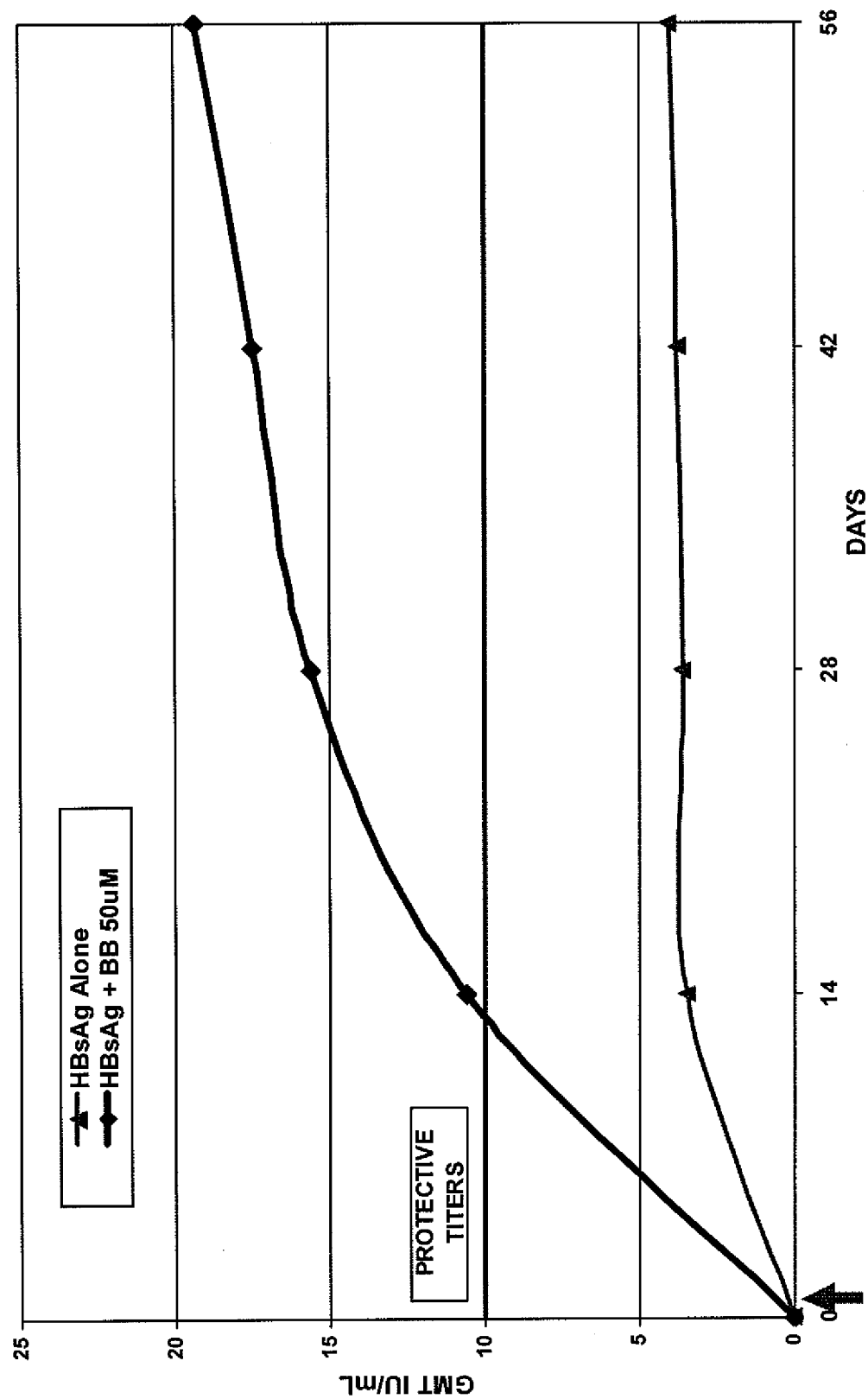
FIG. 3 Neutralising antibody titers following immunization with Hepatitis-B vaccine as per present invention. (Better and sustained antibody titer providing to sero-protection)

3 Wistar rats per group were randomized and were immunized with single injection of 10 microgram of HBsAg with BB 50 uM as adjuvant. The rats were bled were $14^{th}$ day after immunization and antibody titers were analysed by ELISA. The results of this study are presented in FIG. 3.

Example 4

Figure 4:
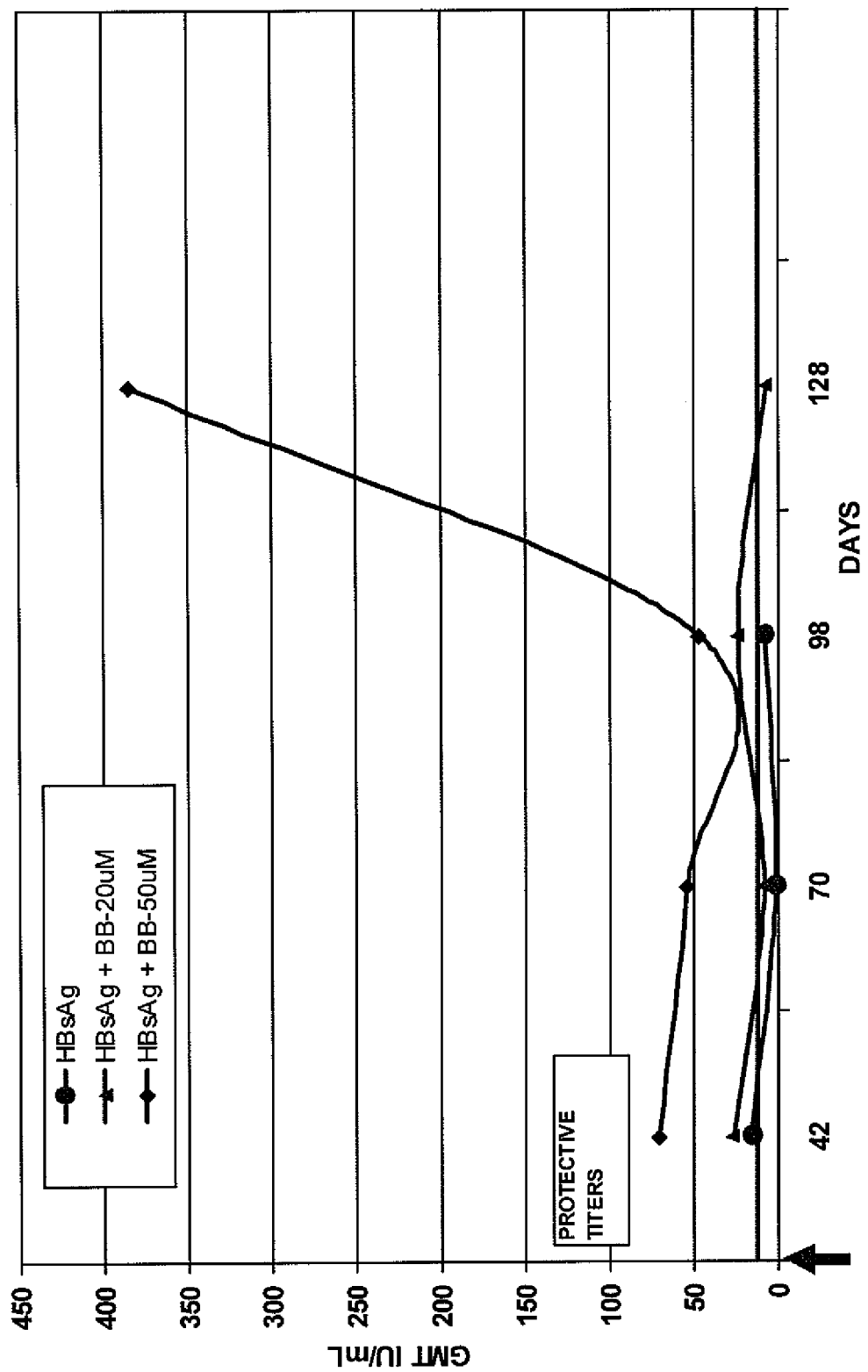
FIG. 4 Neutralising antibody titers following immunization with Hepatitis-B vaccine as per present invention. (Higher and sustained antibody response leading to long lasting sero-protection)

Wistar rats/3 per group were immunized with rHBsAg antigen mixed with 20 μM and 50 μM of BB. Each Rat was injected with 10 μg, on day 0, intramuscular injection. Anti-HBsAg antibodies were detected in individual rat serum at every 14 days interval. BB-50 uM BB-5 uM are lead adjuvants. The results of this study are presented in FIG. 4.

Example 5

5 mice in each group were immunized with inactivated rabies virus (Rabipur) adjuvanted with/without BB as adjuvant, third group was immunized with PBS as control. Single immunization was done on day 1. The mice were bled on day 0, 7, & 14 and the antibodies were measured using ELISA kit from BioRAD.

Figure 5:
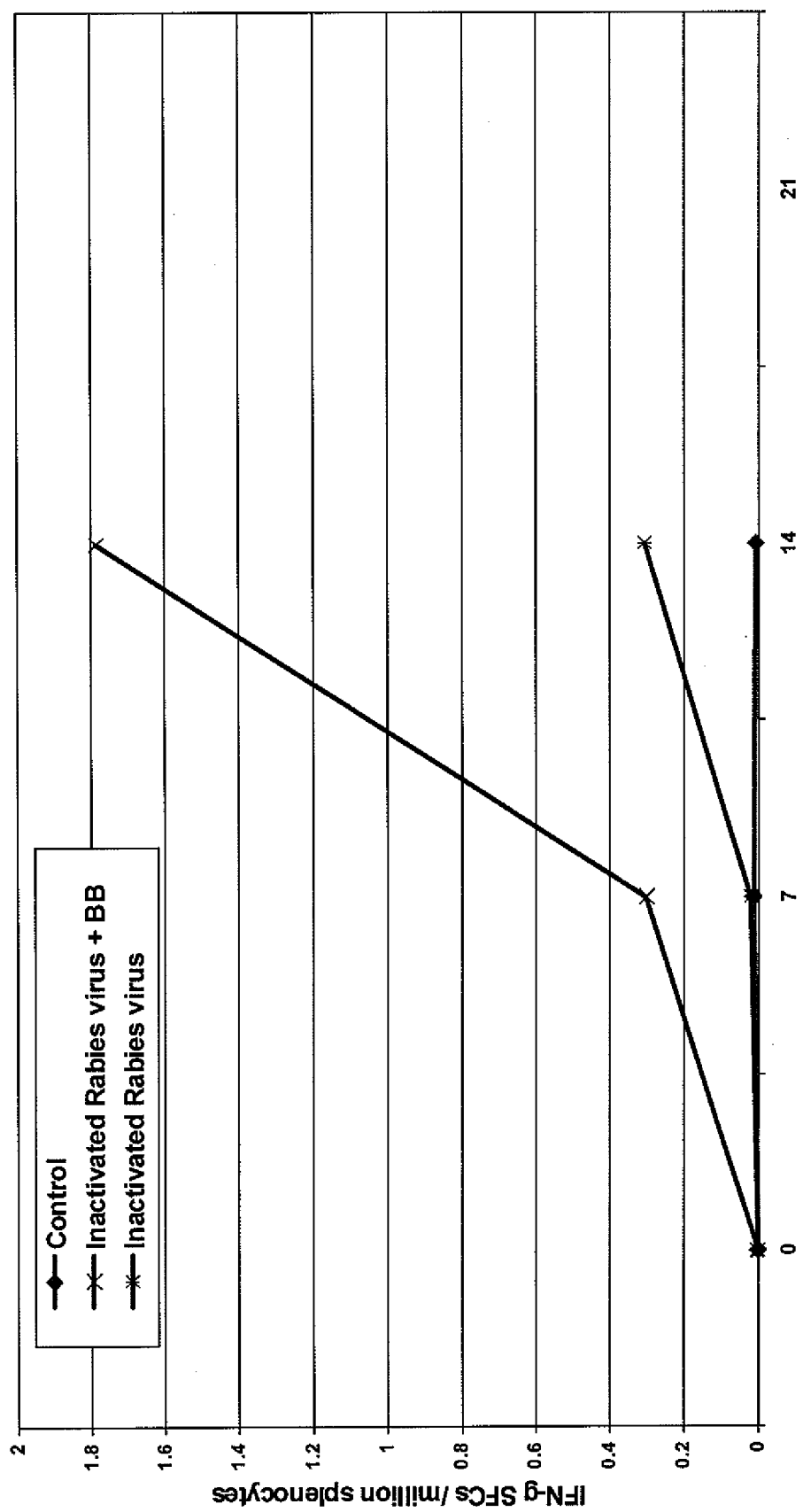
FIG. 5 Neutralising antibody titers following immunization with inactivated rabies virus vaccine. Sero-conversion with higher antibody response)

The Mice immunized with BB as adjuvant along with rabies vaccine produced faster and stronger response. The titers were protective on day 14. The results of this study are presented in FIG. 5.

Example 6

Recombinant NE protein (1 μg) of hepatitis E virus mixed with 5 μM of BB and was administered intramuscularly. 60% sero-conversion was seen on day 14 after 1st injection and 100% after 2nd injection given 2 weeks later.

Example 7

5 mice in each group were immunized with cancer cells (Mia-paca 2) with/without BB as adjuvant, third group was immunized with PBS as control. Two immunization doses were given on day 1 and day 21. The mice were sacrificed on day 28 the splenocytes were removed and interferon gamma (IFN-g) ELISPOT was performed.

Figure 6:
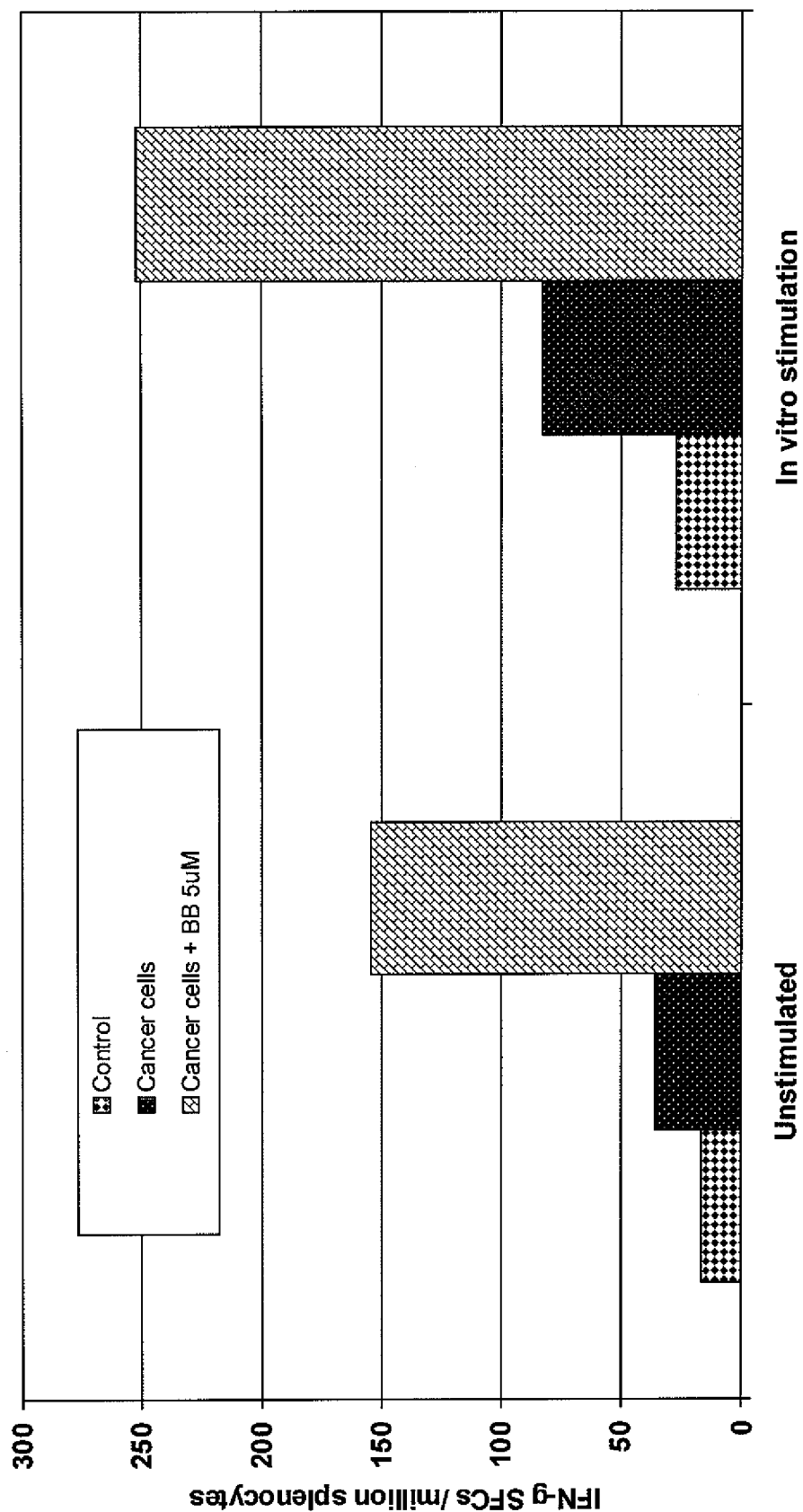
FIG. 6 Cell mediated immune response following immunization with cancer vaccine as per present invention.

The Mice immunized with BB as adjuvant along with cancer cells produced more then three times greater response then the mycobacterium adjuvanted group. The results of this study are presented in FIG. 6. The type of immune response generated is fount of result in reduction of tumor size.

The present invention provides FXR antagonist as an adjuvant and pharmaceutical composition containing the same along with antigen.

We claim:

1. A method of modulating immune response by administering a therapeutically effective amount of an antigen and an adjuvant wherein the adjuvant is farnesoid-X-receptor (FXR) antagonist.

2. A method according to claim 1, wherein the FXR antagonist is selected from the group consisting of a 3βHydroxy-5,16-pregnadien-20-one, a Guggulipid, a Guggulsterone, a 3β-Acetoxypregna-5,16-dien-20-one(16-DPA), a 4,16-Dien-pregna-3,20-dione, a 3β-Actoxypregna-5-en-20-one, a 3β-Hydroxypregna-5-en-20-one, a 5,16-Dien-pregnane-3,20-diol, a 5,17(20)-Dien-pregna-3,16-diol-diacetate, a 5,17(20)-Dien-pregna-3,16-diol, a 3β-Hydroxypregna-5,16-dien-20-one, a 7-(2-Hexyloxy-3,5-diisopropyl-phenyl)-3-methyl-octa-2,4,6-trienoic acid, a Z-Guggulsterone, a [4,17(20)-Cis-pregnadiene-3,16-dione], an E-Guggulsterone and a [4,17-(20)-Trans-pregnadiene-3,16-dione] and a combination thereof.

3. The method of claim 1, wherein the amount of said FXR antagonist ranges from about 10 nM to about 1 mM.

4. The method of claim 1, wherein the amount of said FXR antagonist ranges from about 1 µM to about 100 µM.

5. The method of claim 1, wherein the amount of said FXR antagonist ranges from about 1 µM to about 50 µM.

* * * * *